(12) United States Patent
Chan et al.

(10) Patent No.: US 9,465,032 B2
(45) Date of Patent: Oct. 11, 2016

(54) METHOD OF USING ANTIBODY-LIPOSOME COMPLEXES FOR SELECTING A POOL OF MOLECULES

(71) Applicants: SCINOPHARM TAIWAN LTD., Tainan (TW); NATIONAL YANG-MING UNIVERSITY, Taipei (TW)

(72) Inventors: Hardy W. Chan, Redwood City, CA (US); Chi-Ying Huang, Taipei (TW)

(73) Assignees: SCINOPHARM TAIWAN LTD., Shan-Hua (TW); NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 14/376,515

(22) PCT Filed: Dec. 4, 2012

(86) PCT No.: PCT/IB2012/003117
§ 371 (c)(1),
(2) Date: Aug. 4, 2014

(87) PCT Pub. No.: WO2014/087191
PCT Pub. Date: Jun. 12, 2014

(65) Prior Publication Data
US 2015/0037317 A1 Feb. 5, 2015

(51) Int. Cl.
| | | |
|---|---|---|
| *G01N 33/10* | (2006.01) | |
| *G01N 33/543* | (2006.01) | |
| *G01N 33/574* | (2006.01) | |

(52) U.S. Cl.
CPC .... *G01N 33/57492* (2013.01); *G01N 33/5432* (2013.01); *G01N 2500/10* (2013.01)

(58) Field of Classification Search
CPC .................. G01N 33/5432; G01N 33/57492; G01N 2500/10
See application file for complete search history.

(56) References Cited

U.S. PATENT DOCUMENTS

| | | |
|---|---|---|
| 4,859,765 A | 8/1989 | Nestor, Jr. et al. |
| 5,248,590 A | 9/1993 | Rutner et al. |
| 5,278,045 A | 1/1994 | Tam |
| 7,780,882 B2 | 8/2010 | Chang et al. |
| 2004/0067599 A1 | 4/2004 | Katz et al. |
| 2005/0196755 A1 | 9/2005 | Zauderer et al. |
| 2010/0119593 A1 | 5/2010 | Liao et al. |
| 2011/0236957 A1 | 9/2011 | Weng |

FOREIGN PATENT DOCUMENTS

| | | |
|---|---|---|
| KR | 10-2009-0063924 A | 6/2009 |
| WO | 98/28623 A1 | 7/1998 |
| WO | 2006/012522 A1 | 2/2006 |

OTHER PUBLICATIONS

English-language version of an Action dated Jul. 29, 2015 for Application No. EP 12 889 551.3-1405.
Obrist, R., "Monoclonal antibodies as drug carriers in oncology", Trends in Pharmacological Sciences, Elsevier, Sep. 1983, pp. 375-379.
Action and Search Report with English translation dated Apr. 24, 2015 for Taiwan Application No. 102144481.
Yoshinori Sohma et al., "Recognition of liposome-bound antigens by antipeptide antibody", Applied Biochemistry and Biotechnology, 1993, vol. 38, Issue 3, pp. 179-188.
Salvadori LG et al., "Group a *Streptococcus*-liposome ELISA antibody titers to group a polysaccharide and opsonophagocytic capabilities of the antibodies", The Journal of Infectious Diseases, 1995, vol. 171(3), pp. 593-600.
Kimberley Laginha et al., "Liposomes targeted via two different antibodies: Assay, B-cell binding and cytotoxicity", Biochimica et Biophysica Acta, 2005, vol. 1711, pp. 25-32.
JP Hughes et al., "Principles of early drug discovery", British Journal of Pharmacology, 2011, vol. 162, pp. 1239-1249.
Wynne Aherne et al., "Mechanism-Based High-Throughput Screening for Novel Anticancer Drug Discovery", Anticancer Drug Development, 2002, pp. 249-267.
Blonder, Josip, et al., Enrichment of integral membrane proteins for proteomic analysis using liquid chromatography-tandem mass spectrometry, Journal of Proteome Research, 2002, 1(4): p. 351-360.
Han, David K., et al., Quantitative profiling of differentiation-induced microsomal proteins using isotope-coded affinity tags and mass spectrometry. Nature Biotechnology, 2001, 19(10): p. 946-951.
Nobs, Leila, et al., Current mehtods for attaching targeting ligands to liposomes and nanoparticles. Journal of Pharmaceutical Sciences, 2004. 96(8): p. 1980-1992.
Koebek, Petra, et al., Targeting cancer cells using PLGA nanoparticles surface modified with monoclonal antibody. Journal of Controlled Release, 2007. 120(1-2): p. 18-26.
Liu, Yen Ka, et al., A unique and potent protein binding nature of liposome containing polyethylenimine and polyethylene glycol: a nondisplaceable property. Biotechnology and Bioengineering, 2011. 108(6): p. 1318-1327.
European Search dated Nov. 4, 2014 for Application No. EP 12889551.3-1405.
Liao, Kuang-Wen, et al. "Liposome-based polymer complex as a novel adjuvant: enhancement of specific antibody production and isotype switch", International Journal of Nanomedicine, Feb. 1, 2012, pp. 607-621.
Search Report dated Dec. 18, 2015 for Chinese Application 201280074284.8.

(Continued)

*Primary Examiner* — Robert Landsman
(74) *Attorney, Agent, or Firm* — Ladas & Parry LLP

(57) ABSTRACT

The present disclosure relates to a method for selecting a pool of molecules comprising detecting if the pool of molecules has binding specificity to an agent. A method for selecting a pool of biological markers in or on a cell, a composition comprising a pool of molecules, a method for delivering a therapeutic agent, and a method for diagnosing a condition in a subject are also provided.

13 Claims, 7 Drawing Sheets

(56) References Cited

OTHER PUBLICATIONS

Office Action dated Dec. 28, 2015 for Chinese Application 201280074284.8.
Liu, Yen-Ku, et al., A Unique and Potent Protein Binding Nature of Liposome Containing Polyethylenimine and Polyethylene Glycol: A Nondisplaceable Property, Biotechnology and Bioengineering, vol. 108, No. 6, Jun. 6, 2011, pp. 1318-1327.
Office Action dated Feb. 10, 2016 for EP Application No. 12 889 551.3.
Korean Patent Abstracts English abstract of KR 10-2009-0063924 A.
Lee, C. M. Y., et al., "Selection of human antibody fragments by phage display", Nature Protocols, vol. 2, No. 11, 2007, pp. 3001-3008.
Francis, G. D., et al., "Prediction of histologic grade in breast cancer using an artificial neural network", IEEE World Congress on Computational Intelligence, Jun. 10-16, 2012, pp. 1-5.

METHOD OF USING ANTIBODY-LIPOSOME COMPLEXES FOR SELECTING A POOL OF MOLECULES

RELATED APPLICATION INFORMATION

This application is a 371 of International Application PCT/IB2012/003117 filed 4 Dec. 2012 entitled "Method for Selected a Pool of Molecules", which was published in the English language on 12 Jun. 2014 with International Publication Number WO 2014/087191 A1, the content of which is incorporated herein by reference.

FIELD OF THE INVENTION

This invention relates to a method for selecting a pool of molecules. More particularly, the invention relates to a method for selecting a pool of molecules that have high selectivity for certain biological markers of interests.

BACKGROUND OF THE INVENTION

Interactions between molecules are necessary for all bio-reactions. The interactions between antibodies and antigens, and ligands and receptors are crucial for initiating a series of pathways to response to external stimuli. Identification of a specific molecule involved in the interactions is very important to research and pharmaceutical development.

For example, after the completion of the human genomic project, most human expressed genes have been identified. However, in the emerging proteomics era, proteins act as key players in the unveiling of these genes. In order to effectively decipher the mystery of these proteins, many efforts have been taken to generate at least one antibody to every human expressed gene in the human genome. Antibodies with their inherent sensitivity and specificity thus become the most versatile tools for providing one-to-one relationship with their target proteins. However, one of the complexities is that these proteins do not always behave in the same way when placed in different (e.g. cancer) cells. Many proteins are known for their translocation capability in different cell contexts; thus the corresponding antibodies will recognize distinct locations in a given cell. Moreover, in many cases, protein translocations are involved in the activation of tumor cells. Detecting the movements might help diagnose the type and stage of cancer in the future. The high-throughput approach with direct selection of antigen on the cell membrane may allow the discovery of potential therapeutic targets and new disease markers.

However, while numerous useful antibodies have been generated, the main limitations are two folds, namely (1) how to directly uncover specific antigens (e.g. membrane or surface markers) in a given cell and (2) how to rapidly identify the valuable antibodies recognizing these antigens.

Taking membrane proteins as an example, many membrane proteins are implicated in particular disease states, such as lung cancer, and often are attractive therapeutic targets. Systematic and quantitative profiling of membrane proteins may facilitate our understanding of their roles in regulating biological processes in various disease states. Approximately 20 to 30% of open reading frames of most sequenced genomes are estimated to encode integral membrane proteins (Blonder, J., et al., *Enrichment of integral membrane proteins for proteomic analysis using liquid chromatography-tandem mass spectrometry*. Journal of Proteome Research, 2002. 1(4): p. 351-360; Han, D. K., et al., *Quantitative profiling of differentiation-induced microsomal proteins using isotope-coded affinity tags and mass spectrometry*. Nature Biotechnology, 2001. 19(10): p. 946-951). However, the membrane proteome has not been mapped and is experimentally challenging because of the low abundance of membrane proteins. Moreover, using high-throughput proteomics and microarray-based screening studies, the identified novel targets often lack antibodies for characterization of their location and function, further preventing researchers from pursuing potential membrane proteins. A direct expression profiling method for identifying antibodies and recognizing receptors (surface markers or membrane-associated proteins) is essential.

Random screening is time-consuming and usually impracticable due to the various physiological conditions. Using individual antibodies to screen new receptors is impossible due to the requirement of more than 25000 antibodies to cover the whole genome. Moreover, cancer cells often have multiple overexpressed receptors and distinct cell types that may have different location profiles for the same target protein. Therefore, it is necessary to develop a rapid and effective method to address these questions at the same time.

SUMMARY OF THE INVENTION

The invention is to provide a method of small pool expression screening for selecting a pool of molecules having high selectivity for certain biological markers of interests.

The invention is to provide a method for selecting a pool of molecules comprising detecting if the pool of molecules has binding specificity to an agent.

The present invention is also to provide a method for selecting a pool of biological markers in or on a cell, which comprises the method as mentioned above, wherein the pool of molecules is the pool of biological markers.

The present invention is also to provide a composition comprising a pool of molecules selected according to the method as mentioned above.

The present invention is also to provide a method for delivering a therapeutic agent comprising administrating the composition as mentioned above to a cell or a subject.

The present invention is also to provide a method for diagnosing a condition in a subject comprising providing a biological sample; contacting the composition as mentioned above with the biological sample; and identifying whether the composition binds with the biological sample, wherein the presence of the binding indicates that the subject is afflicted with the condition.

The present invention is described in detail in the following sections. Other characteristics, purposes and advantages of the present invention can be easily found in the detailed description and claims.

DETAILED DESCRIPTION OF THE INVENTION

Figure 1:
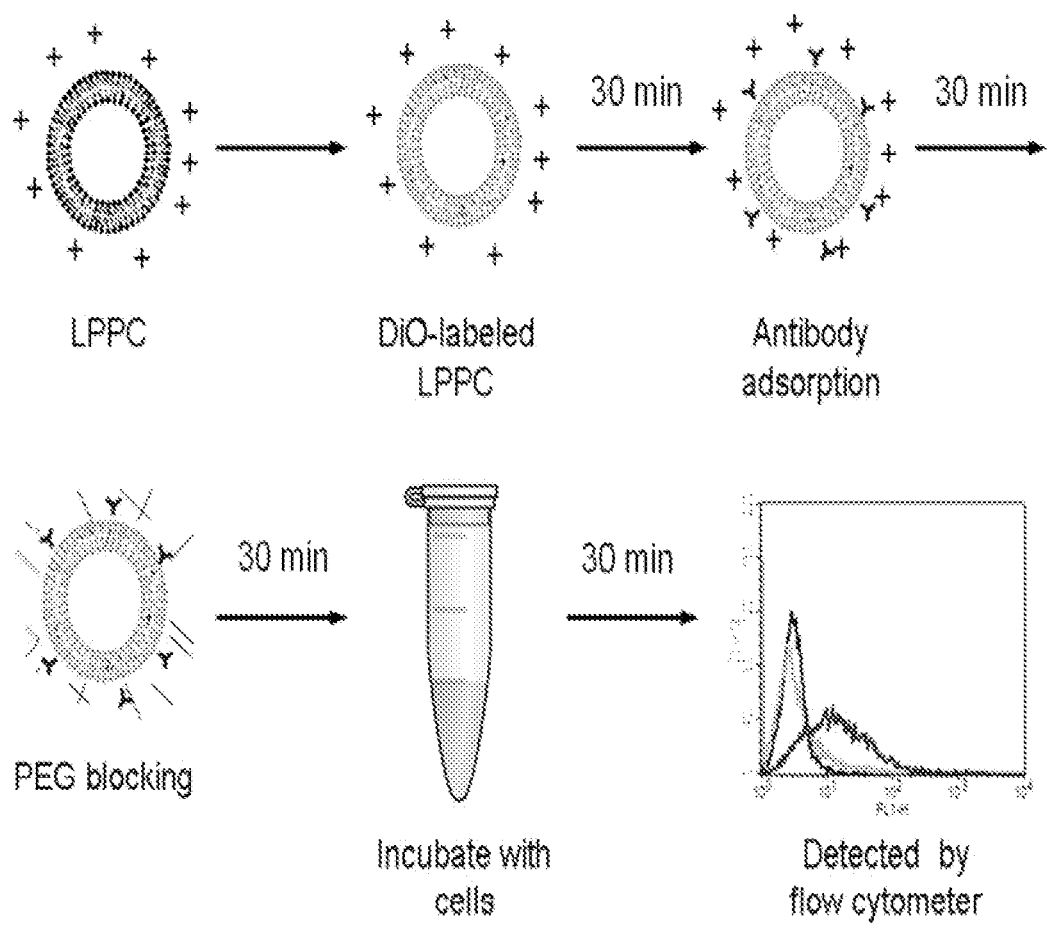
FIG. 1: Schematic illustration of LPPC (Liposome/PEI/PEG complex) adsorption with antibody-targeting cancer cells. Antibodies were mixed with DiO-labeled LPPCs, followed by blocking with PEG1500. Complexes of PEG-blocked LPPC/antibodies were incubated with cells (e.g., A549) and then analyzed by FACScan flow cytometry to determine their binding efficiencies to the cell surface. The fluorescent mean of each sample was normalized to a positive control (100% DiO-labeled LPPC on cells) and a negative control (unbound antibody). The fluorescent mean of each sample was first divided by the fluorescent mean of the positive control. Subsequently, the normalized values were divided by the fluorescent mean of the negative control.

The invention provides a method for selecting a pool of molecules comprising detecting if the pool of molecules has binding specificity to an agent.

As used herein, the term "molecule" refers to a small molecule or a macromolecule involved in a biochemical reaction. Preferably, the molecule is a macromolecule such as a protein, peptide, nucleotide, oligonucleotide or poly nucleotide. The molecule can be natural or artificial. In another aspect, the molecule can be purified or mixed with other contents. In one preferred embodiment of the invention, the expression pattern of the molecule is different in a normal condition and in an abnormal condition, such as a disease. In another preferred embodiment of the invention, the expression pattern of the molecule is different in different cell types. In yet another preferred embodiment of the invention, the molecules are antibodies, antigens, enzymes, substrates, ligands, receptors, cell membrane-associated proteins or cell surface markers. In one further preferred embodiment of the invention, the molecules are antibodies.

As used herein, the term "a pool of molecules" refers to a group of molecules where the molecules can be the same or different.

As used herein, the term "agent" refers to a small molecule or a macromolecule involved in a biochemical reaction. Preferably, the agent is a macromolecule such as a protein, peptide, nucleotide, oligonucleotide or poly nucleotide. The agent can be natural or artificial. In another aspect, the agent can be purified or mixed with other contents. Preferably, the agent is located in or on a cell. In one preferred embodiment of the invention, the expression pattern of the agent is different in a normal condition and in an abnormal condition, such as a disease. In another preferred embodiment of the invention, the expression pattern of the agent is different in different cell types. In yet another preferred embodiment of the invention, the agent is an antibody, antigen, enzyme, substrate, ligand, receptor, cell membrane-associated protein or cell surface marker. In one further preferred embodiment of the invention, the agent is an antigen.

As used herein, the term "binding specificity" refers to a property that even when different molecules are present, only the molecules that have the specific shape complementary to the active site are able to bind to the agent's active site.

For easy manipulation, the pool of molecules is preferably located onto a vehicle. The manner of locating the pool of molecules can be naturally occurring or artificially binding the pool of molecules to the vehicle. According to the types of the vehicles and the molecules, artisans' skills in this field can choose suitable manner to achieve the binding. For example, U.S. Pat. No. 7,780,882 discloses a method of preparing an antibody- or antibody fragment-targeted cationic immunoliposome or polymer complex. Such disclosure is incorporated herein as reference. In one embodiment of the invention, the vehicle is a liposome, a micelle, a timed released capsule, a vesicle, a microspheres, a nanoparticle, a polyplex or a cell; preferably, a liposome.

Most of the currently available liposomes are manufactured by covalently conjugating targeting molecules onto liposome components, such as cholesterols or polymer-modified lipid side chains. The coupling reaction may dramatically damage the activity of certain targeting molecules (Nobs, L., et al., *Current methods for attaching targeting ligands to liposomes and nanoparticles*. Journal of Pharmaceutical Sciences, 2004. 93(8): p. 1980-1992; Kocbek, P., et al., *Targeting cancer cells using PLGA nanoparticles surface modified with monoclonal antibody*. Journal of Controlled Release, 2007. 120(1-2): p. 18-26). One way to avoid this problem involves the non-covalent adhesion of targeting molecules to the cationic liposome. However, the dissociation of targeting molecules from the liposomes poses another problem for influencing the activity of the liposome (Nobs, L., et al.). This is mainly because of the weak interaction between the targeting molecules and liposomes. Recently, a liposomal vector, LPPC (Liposome/PEI/PEG complex), has been developed that can not only be conveniently loaded with anti-tumor drugs, but can also strongly adsorb tumor specific antibodies on its surface, allowing the particle to be directed to cancer cells (Liu, Y. K., et al., *A unique and potent protein binding nature of liposome containing polyethylenimine and polyethylene glycol: a nondisplaceable property*. Biotechnology and Bioengineering, 2011. 108(6): p. 1318-1327). In addition, the LPPC can be isolated by centrifugation, allowing the LPPC/antibody complex to be easily purified from the unbound antibodies. The empty LPPC can be easily incorporated with fluorescent dyes to form a fluorescent nanoparticle, which offers the potential for the development of a specific probe, with the fluorescent LPPC adsorbing to specific antibodies.

As used herein, the cell is preferably a normal cell, a cancer cell, a stem cell, or a cancer stem cell. The specifically binding between the molecule and the agent preferably occurs in the cell in a physiological condition or in vivo.

For easy manipulation, the vehicle preferably comprises a detectable marker. According to the types of the vehicle and the detectable marker, artisans' skills in this field can choose suitable manner to tag the vehicle to the detectable marker. In one preferred embodiment of the invention, the detectable marker is fluorescence or a radioisotope.

In order to apply the method, according to the invention in other aspects such as drug delivery, the vehicle preferably further comprises at least one of a drug, a cytotoxic drug, a growth factor, a cytokine, a vaccine and an oligonucleotide.

Preferably, the method according to the invention further comprises identifying the molecules. Artisans skilled in this field can apply suitable chemical, physical or biological analysis to identify the molecules.

In one preferred embodiment of the invention, the method comprises the steps of:
 (a) providing a pool of candidate molecules;
 (b) dividing the pool of candidate molecules into multiple sub-pools;
 (c) loading each of the sub-pools onto a vehicle to form a complex; and
 (d) contacting the complex obtained in (c) and the agent to detect if the sub-pool comprises the molecules having binding specificity to the agent, whereby the pool of molecules can be selected.

As used herein, the term "candidate molecules" refer to a group of molecules that are suspected to be the molecules the invention is seeking. The pool of candidate molecules can be a naturally extract or an artificial combination, such as a pool of hybridomas that expresses antibodies.

The condition of step (d) of contacting is preferably equivalent to a physiological one. Artisan skilled in this field is able to choose a suitable condition.

In one preferred embodiment of the invention, the method further comprises dividing the sub-pool to additional sub-pools after step (b). This step and steps (b), (c) and (d) can be repeatedly performed to narrow down the number of molecules in the pool.

Preferably, the step (d) further comprises contacting the complex obtained in (c) and a cell to detect if the complex binds to the cell, wherein the agent is located in or on the cell. As used herein, the cell is preferably a normal cell, a cancer cell, a stem cell, or a cancer stem cell. The specifically binding between the molecule and the agent preferably occurs in the cell in a physiological condition or in vivo.

Preferably, the step (d) further comprises contacting the complex obtained in (c) and a cell to detect if the complex kills the cell, wherein the agent is located in or on the cell. As used herein, the cell is preferably a cancer cell.

According to the invention, the small pool concept is provided to identify "mixed-pool antibodies" to reveal new receptors overexpressed in given cells, e.g., cancer cells and stem cells. The underlying concept is subdivision of the whole antibody library into smaller pools to substantially increase the probability of detecting potential receptors (surface markers or membrane-associated proteins) for a given cancer cell type. This method makes it easier to rapidly isolate a single antibody once a candidate pool antibody is identified. Moreover, unlike other proteomics and microarray-based screening studies where the identified targets often lack antibodies necessary for demonstrating their location in the membrane, our approach identifies novel antibody-recognizing receptors and can be immediately employed in various applications.

The present invention is also to provide a method for selecting a pool of biological markers in or on a cell, which comprises the method mentioned above, wherein the biological markers are tumor specific antigens, cell membrane-associated proteins or cell surface markers.

The present invention is also to provide a composition comprising a pool of molecules selected according to the method as mentioned above.

The present invention is also to provide a method for delivering a therapeutic agent comprising administrating the composition as mentioned above to a cell or a subject.

The present invention is also to provide a method for diagnosing a condition in a subject comprising providing a biological sample; contacting the composition as mentioned above with the biological sample; and identifying whether the composition binds with the biological sample, wherein the presence of the binding indicates that the subject is afflicted with the condition.

Preferably, the biological sample is a cancer cell, a cancer stem cell, a tumor biopsy or a tissue culture.

Preferably, the subject is a human.

There are many potential applications of the method according to the invention. In one embodiment of the invention, this screening is identification of differentially expressed disease-related receptors by comparing normal and diseased cells. By conjugating liposomes with one or multiple antibodies, the tumor cells can receive a relative high dosage of drugs when compared with normal tissues, providing an alternative treatment strategy. The identified receptor may be used for drug delivery via, for example, the liposome.

In another embodiment of the invention, the identification of specific cell-surface markers is performed in other situations. For example, this approach can be used to identify surface markers for stem cell research, e.g., in mesenchymal stem cells (MSCs), neural stem cells (NSCs), pluripotent stem cells and cancer stem cells, and to identify cell-type specific differentiation markers. The single or multiple identified surface marker(s) may be used to identify and isolate cells (or subpopulations) of interest from a heterogeneous pool. In other words, the identified cell-surface markers can be used for cell analysis and sorting via, for example, flow cytometry.

In yet another embodiment of the invention, the method is rapid characterization of potential receptors (surface markers or membrane-associated proteins) from large collections of monoclonal or polyclonal antibodies, generated from peptides or phage display. In general, there is a lack of systematic analysis methods for unraveling potential receptors from these antibody inventories. Using small pool-based antibody expression screening, it is possible to scan thousands of antibodies within a short period of time.

The following examples are provided to aid those skilled in the art in practicing the present invention.

EXAMPLES

Methods
Cells Incubated with LPPC/Antibody Complexes

In this example, the LPPC (Liposome/PEI/PEG complex) was labeled with green fluorescence dye DiO for 30 minutes. Next, 20 µg of DiO-labeled LPPC was incubated with 1 µg of an antibody pool of 9 antibodies for 30 minutes. LPPC/antibody complexes were then blocked with PEG1500 for 30 minutes and centrifuged at 5,900×g for 5 minutes to remove excess PEG. Finally, PEG-blocked LPPC/antibody complexes were incubated with $3\times10^5$ cells for 30 minutes to allow for binding with antigens on the cell surface. The binding efficiency was measured by FACScan flow cytometry. The fluorescent mean of each sample was normalized using a positive control (100% DiO-labeled LPPC on cells) and a negative control (unbound antibody). The fluorescent mean of each sample was first divided by the fluorescent mean of the positive control. Subsequently, the normalized values were divided by the fluorescent mean of the negative control; the cut off was a 3-fold change for classification as a positive result.

Immunofluorescence

To characterize the localization of selected proteins, cells were stained with antibody by immunofluorescence. Cells were washed with phosphate-buffered saline (PBS) and fixed with 3.7% formaldehyde in PBS for 5 minutes at 25° C., followed by washing with PBS 3 times for 10 minutes. Cells were permeabilized for 5 minutes in PBS containing 0.5% Triton X-100 and were blocked in 5% normal goat serum for 30 minutes. The fixed cells were probed with primary antibody (e.g., SPAG5) in PBS with 1% normal goat serum at 4° C. overnight. DNA was stained with 4,6-diamidino-2-phenylindole (DAPI, 2 µg/ml). Immunofluorescent cell images were acquired using an Olympus LSM Fluoview FV1000 confocal laser-scanning microscope (Olympus).

Results
Establishing LPPC/Antibody Complexes for Screening Novel Receptors and Membrane-Associated Proteins The LPPC/antibody complex is easily purified from unbound antibodies. In addition, the empty LPPCs can be easily incorporated with fluorescent dyes to form fluorescent nanoparticles, which offer the potential for the development of specific probes, with the fluorescent LPPC adsorbing specific antibodies. The antibody/fluorescent LPPC complex serves as a good tool for detection of surface antigens without chemical conjugation. The binding efficiency can be measured by a FACScan flow cytometer (FIG. 1). These processes can be simply performed and finished in a small test tube, and the results demonstrate that our approach is feasible for the identification of new receptors and/or membrane-associated proteins.

Figure 2:
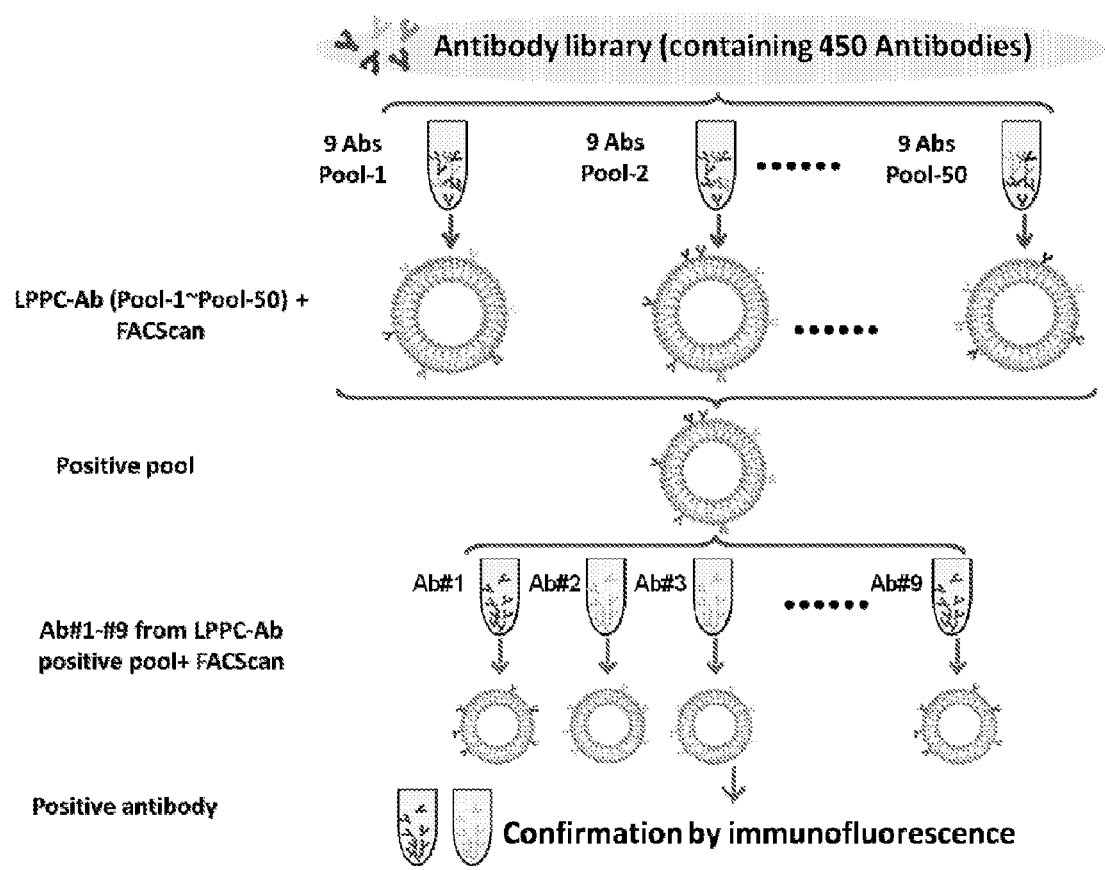
FIG. 2: Schematic illustration of the antibody-based liposome for drug screening. A total of 450 antibodies were separated into 50 pools, and these were used to form liposome-antibody (LPPC/antibody) complexes. To screen antibody binding efficiency to the cell surface, 50 LPPC/antibody complexes were incubated with different cancer cell lines at 4° C. The LPPC/antibody complexes with high efficiency binding to the cell surface were then prioritized by FACScan flow cytometry analysis. Individual antibodies from the selected pool, e.g., pool 3A, were then used to determine their binding efficiencies to the cell surface by incubation with LPPCs, followed by FACScan analysis. Immunofluorescence was used as a secondary screening to confirm the subcellular location of the selected targets.
Figure 3:
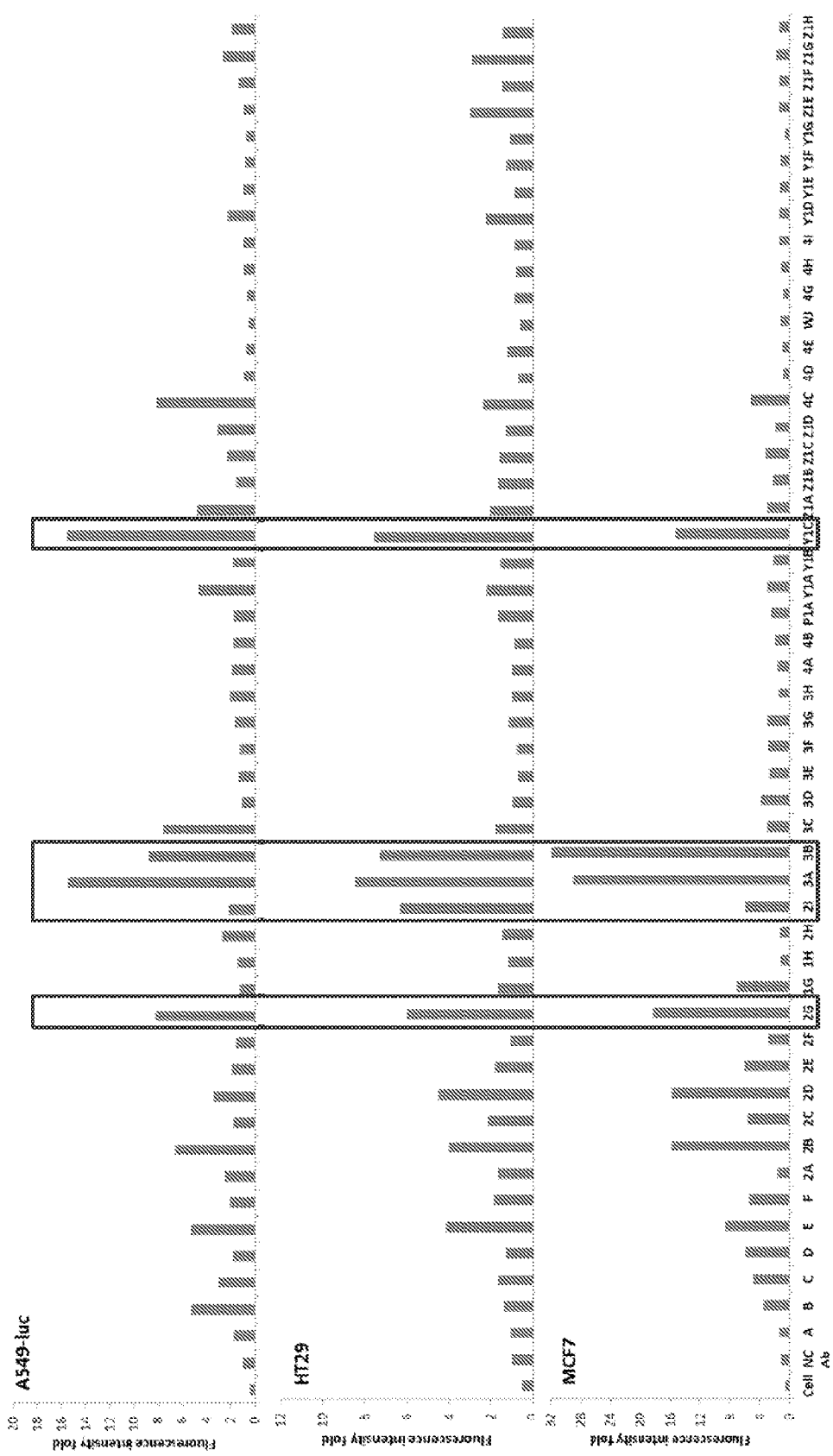
FIG. 3: Screening of liposome-mediated antibody pools to identify specific receptors in different cancer cell lines. Fifty individual antibody pools were mixed with DiO-labeled LPPCs, followed by incubation with 3 different cell lines (A549, HT29, and MCF7) and analysis with FACScan flow cytometry. Five pools (pool 2G, 2I, 3A, 3B and Y1C) exhibited better binding efficiency than the other antibody pools tested. These pools were sub-divided into individual antibodies to test their binding efficiencies with LPPC, as shown in FIGS. 4-7. The "Cell" refers to cell alone without DiO staining. The "NC Ab" refers to unbound antibody on LPPC.
Figure 4:
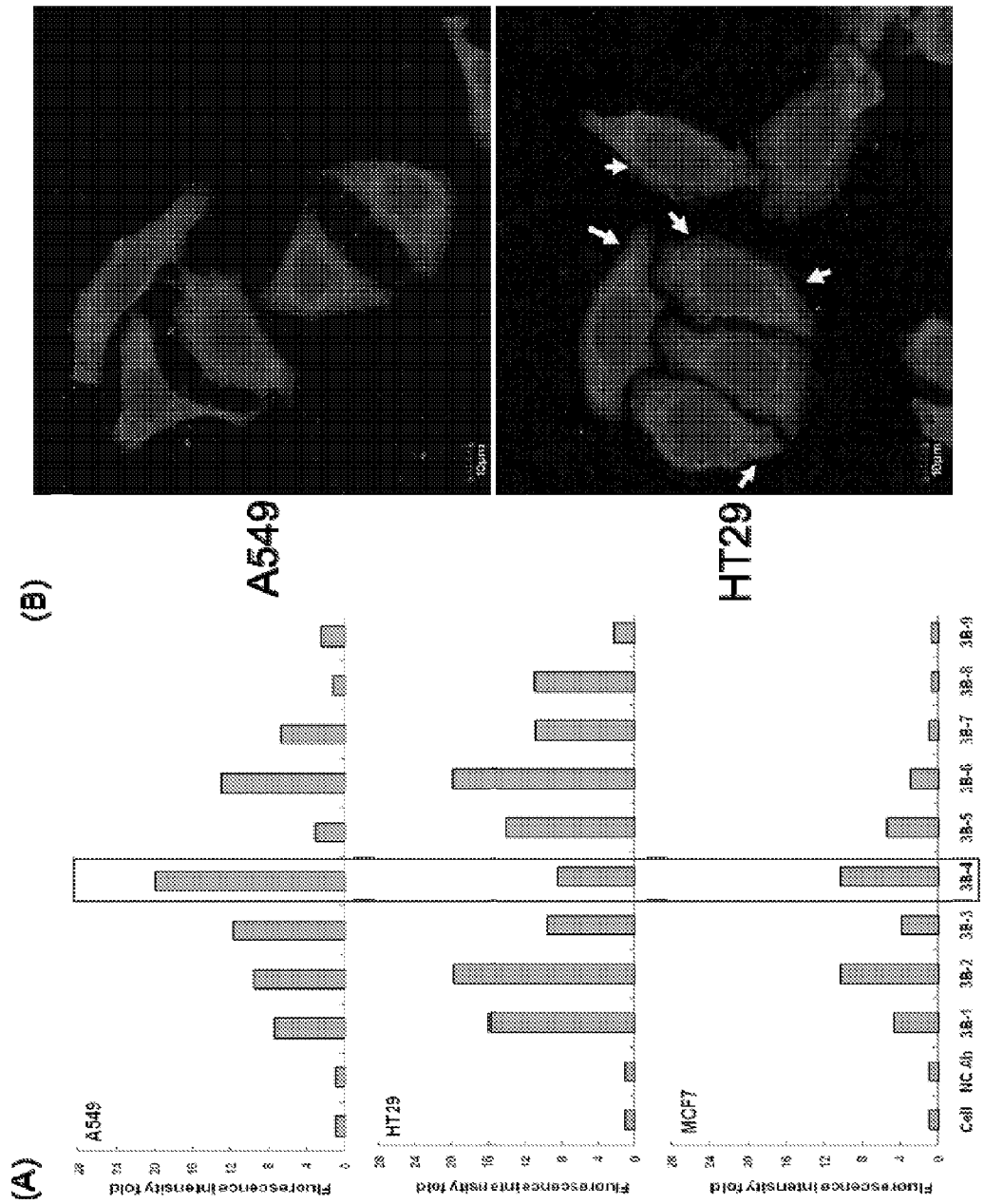
FIGS. 4(A)-4(B): Verification of the subcellular localization of prioritized proteins in pool 3B. (A) Individual antibodies from pool 3B were tested on 3 types of cancer cells using the LPPC/antibody complex system. Many of these antibodies were selected for further verification of their subcellular localization by immunofluorescence. (B) 3B-4 (MAPK8, red) was localized at the plasma membrane in HT29 cells (colon cancer cell line), but not in A549 cells (lung adenocarcinoma cell line).
Figure 5:
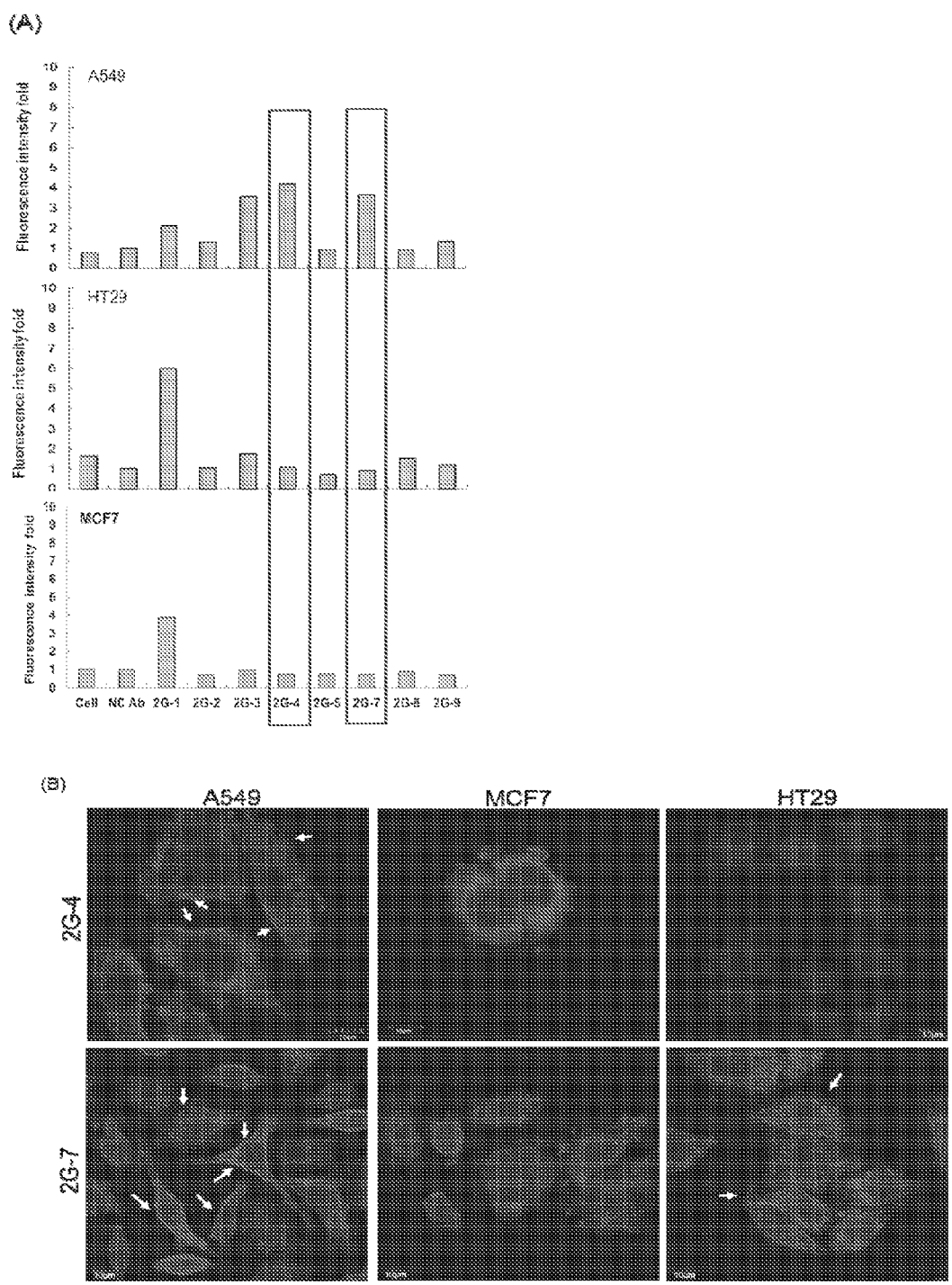
FIGS. 5(A)-5(B): Verification of the subcellular localization of prioritized proteins in pool 2G. (A) Individual antibodies from pool 2G were tested on 3 types of cancer cells using the LPPC/antibody complex system. Many of these antibodies were selected for further verification of their subcellular localization by immunofluorescence. (B) 2G-4 (NUP98, red) was localized at the plasma membrane in A549 cells. 2G-7 (MAG1A9, red) was localized at the plasma membrane in A549 and HT29 cells.
Figure 6:
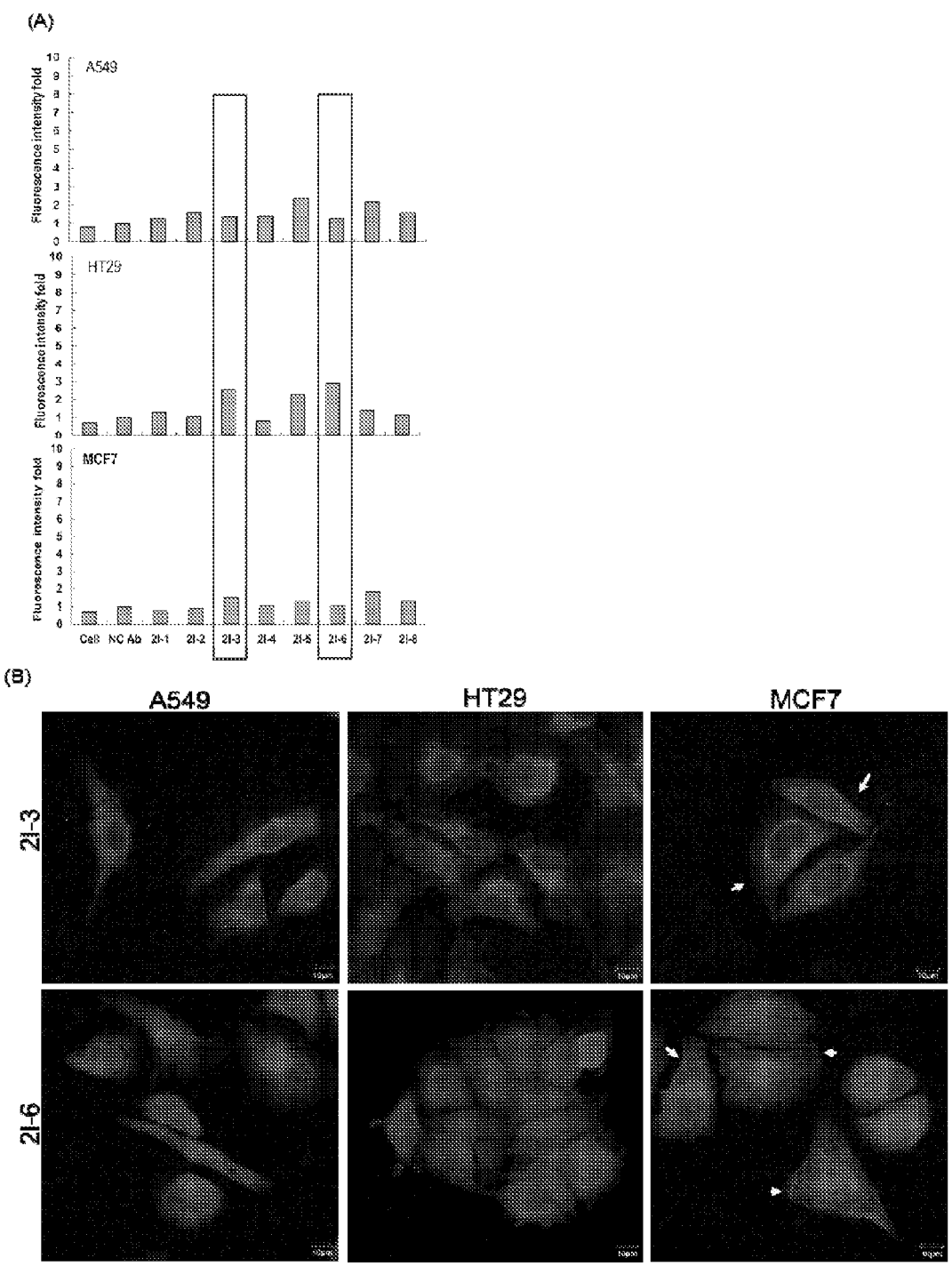
FIGS. 6(A)-6(B) Verification of the subcellular localization of prioritized proteins in pool 2I. (A) Individual antibodies from pool 2I were tested on 3 types of cancer cells using the LPPC/antibody complex system. Two of these antibodies (2I-3 and 2I-6) were selected for further verification of their subcellular localization by immunofluorescence. (B) 2I-3 (PIK3R4, red) and 2I-6 (NPR2, red) were localized at the plasma membrane in MCF7 cells.
Figure 7:
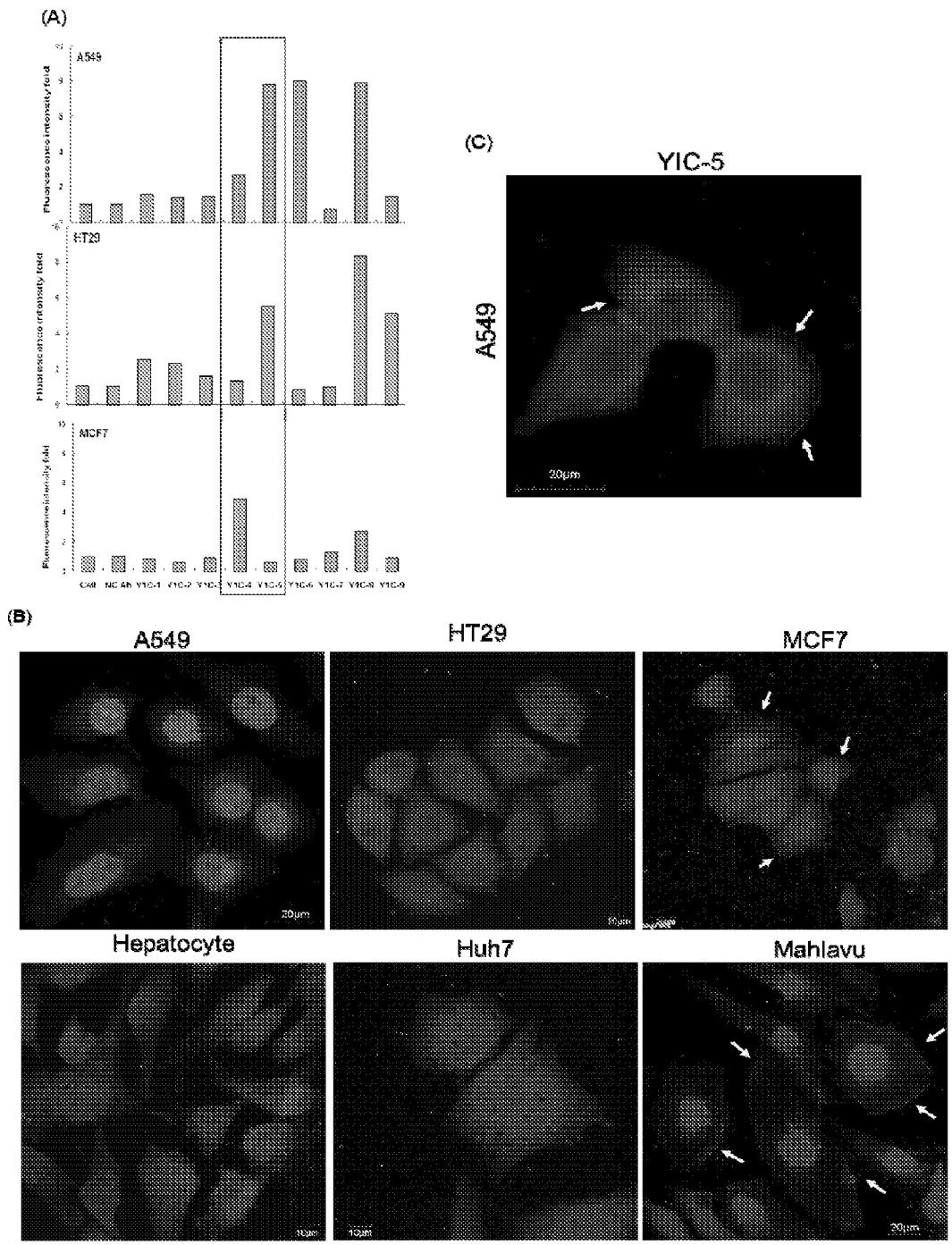
FIGS. 7(A)-7(C): Verification of the subcellular localization of prioritized proteins in pool Y1C. (A) Individual antibodies from pool Y1C were tested on 6 different cell types using the LPPC/antibody complex system. Many of these antibodies were selected for verification of their subcellular localization by immunofluorescence. (B) Y1C-4 (SPAG5, red) was localized at plasma membrane in Mahlavu (hepatocellular carcinoma cell line) and MCF7 (breast cancer cell line) cells, but not in A549 (lung adenocarcinoma cell line), hepatocyte and Huh7 (hepatocellular carcinoma cell line) cells. (C) Y1C-5 (POLR2A, red) was localized at plasma membrane in A549 cells.

Small Pool Antibody Expression Screening for Identification of Cancer-Specific Receptors and/or Membrane-Associated Proteins The question we want to address is whether we can identify receptors (surface markers or membrane-associated proteins) via antibody screening. To demonstrate the feasibility of this idea, we first collected 450 antibodies for this study. Next, 9 antibodies per pool were randomly selected and mixed together prior to loading the fluorescent LPPCs. A total of 50 LPPC-antibody pools were initially incubated with 3 different cell lines: lung cancer (A549), colon cancer (HT29) and breast cancer (MCF7) cells. The antibody-LPPC complexes were then subjected to FACScan analysis (FIG. 2). Based on the results of the primary screening, many pools, including 3A, 3B, Y1C, 2I and 2G, revealed higher membrane-binding abilities in the cancer cells tested than the other pools analyzed (FIG. 3). By carefully examining the subcellular location of each antibody from these 5 selected pools via GO (cellular component) and PubMed searches, we found that each of these 5 selected pools contained known membrane proteins, which, of course, have better membrane-binding efficiencies. However, pool 2I appeared to have different binding efficiencies among the cell lines tested (e.g., the binding efficiency was higher in HT29 cells than in A549 and MCF7 cells). It raised the possibility that different antibodies may have recognized distinct localizations of tested proteins in different cells. Therefore, we postulated that we may be able to identify new receptors and/or membrane-associated proteins from these 5 selected pools, which were selected for further studies, using individual antibodies from each pool (FIGS. 4-7). Thus, after the first run of screening, 9 individual antibodies from a positive pool (e.g., 3A) were tested to determine which antibodies are potential receptors (or membrane-associated proteins) for cancer cells by loading them again onto fluorescent LPPCs (FIG. 2). Several antibodies from these 5 pools, e.g., 3A-9 (or PDGFRB) and Y1C-4 (or SPAG5) (Table 1), not only recovered well known receptors, but also demonstrated the possibility of identifying potential membrane-associated proteins in cancer cells.

Characterizing the Subcellular Localization of Prioritized Proteins from Small Pool Screening Several known receptors were re-discovered in this screening, e.g., 3A-9 (or PDGFRB, see Table 1) and 3B-7 (or KRAS2, see Table 1). Moreover, many antibodies appeared to have distinct affinities toward different cell lines. For example, Y1C-5 had higher affinity to A549 and HT29 cells than to MCF7 cells, whereas Y1C-4 had higher affinity to MCF7 cells than to A549 and HT29 cells. To further validate these observations, we set up a secondary immunofluorescence screening to confirm the membrane localization of the prioritized proteins identified from the initial LPPC screening. To expand the application of this approach, we characterized the subcellular localization of selected targets not only in the initial lung cancer (A549), colon cancer (HT29) and breast cancer (MCF7) cells tested, but also extended the study into other cancer cell lines, including hepatocellular carcinoma cells (Mahlavu). The results showed that 3B-4 (FIG. 4), 2G-4 and 2G-7 (FIG. 5), 2I-3 and 2I-6 (FIG. 6), and Y1C-4 and Y1C-5 (FIG. 7) were localized at the plasma membrane with cell-type specificity. For example, Y1C-4 (or SPAG5, see Table 1) was localized at the plasma membrane in hepatocellular carcinoma cells (Mahlavu) but not in lung cancer cells (A549, FIG. 7).

SPAG5, a mitotic spindle-associated protein, is known to regulate the correct alignment of chromosomes during metaphase, and its expression is involved in breast cancer and non-small cell lung cancer. Moreover, the depletion of SPAG5 caused loss of sister chromatid cohesion. In general, the expression of SPAG5 was very low during interphase and was up-regulated and localized at kinetochores and spindle poles in metaphase. Further studies are needed to dissect the signaling pathway mediated by SPAG5 at the cell membrane in liver cancer. A summary of the immunofluorescence results was shown in Table 1.

TABLE 1

Verification of subcellular localization of the prioritized antibody via immunofluoresence (IF).

| Antibody | Name | Known localization | Tested localization in A549 | Tested localization in MCF7 | Tested localization in HT29 | Note |
|---|---|---|---|---|---|---|
| 3A-6 | BUB1B | nucleus, cytosol | cytosol | cytosol | cytosol, plasma membrane | |
| 3A-9 | PDGFRB | plasma membrane | plasma membrane | plasma membrane | plasma membrane | positive control |
| 3B-4 | MAPK8 | nucleus, cytosol | cytosol | cytosol | cytosol, plasma membrane | |
| 3B-6 | PRKCA | cytosol plasma membrane, | cytosol | cytosol | cytosol | |
| 3B-7 | KRAS2 | plasma membrane, mitochondria | cytosol | cytosol | cytosol plasma membrane, | Positive control |
| Y1C-4 | SPAG5 | nucleus, cytosol | nucleus | nucleus plasma membrane, | nucleus | |
| Y1C-5 | POLR2A | nucleus, nucleoplasm | cytosol, plasma membrane | ND | ND | |
| Y1C-6 | MAD2L1 | nucleus, cytosol | nucleus, cytosol | ND | ND | |
| 2G-3 | IQGAP1 | nucleus, cytosol, plasma membrane | cytosol | cytosol | low expression | |
| 2G-4 | NUP98 | nucleus, nucleoplasm | cytosol, plasma membrane, | cytosol | low expression | |
| 2G-7 | MAG1A9 | unknown | cytosol, plasma membrane | cytosol | cytosol, plasma membrane | |
| 2I-3 | PIK3R4 | cytosol | cytosol | cytosol | cytosol, plasma membrane | |
| 2I-6 | NPR2 | plasma membrane | nucleus, cytosol | nucleus, cytosol | nucleus, cytosol, plasma membrane | |

ND: not determined.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for selecting a pool of molecules comprising the steps of:
    (a) providing a pool comprising a multiplicity of different antibodies;
    (b) dividing the pool of different antibodies into multiple sub-pools with each of the sub-pools comprising a plurality of the different antibodies;
    (c) loading the plurality of different antibodies of the sub-pools onto respective liposomes to form a plurality of complexes, each of the complexes comprising a liposome with a plurality of the different antibodies bound thereto;
    (d) contacting each of the sub-pool complexes with an agent; and
    (e) detecting a sub-pool complex that has the agent bound thereto.

2. The method according to claim 1 further comprising isolating an individual antibody from the sub-pool complex detected in step (e) and testing the individual antibody for binding specificity to the agent.

3. The method according to claim 1, wherein the plurality of different antibodies in each of the sub-pools are mixed together prior to loading onto the respective liposomes.

4. The method according to claim 1, wherein the detecting in step (e) is by flow cytometry.

5. The method according to claim 1, wherein the antibodies are monoclonal antibodies or polyclonal antibodies.

6. The method according to claim 1, wherein the agent is located on a cell, and wherein the cell is a normal cell, a cancer cell, a stem cell, or a cancer stem cell.

7. The method according to claim 1, wherein the agent is an antibody, antigen, enzyme, substrate, ligand, receptor, cell membrane-associated protein or cell surface marker.

8. The method according to claim 1, wherein the liposomes comprise a detectable marker.

9. The method according to claim 8, wherein the detectable marker is fluorescene or radioisotope.

10. The method according to claim 1, wherein the liposomes comprise at least one of a drug, a cytotoxic drug, a growth factor, a cytokine, a vaccine and an oligonucleotide.

11. The method according to claim 1, which further comprises identifying the antibodies bound to the detected sub-pool complex.

12. The method according to claim 1, wherein the agent is located on a cell, and the step (d) comprises detecting if the sub-pool complex binds to the cell.

13. The method according to claim 1, wherein the agent is located on a cell, and the step (d) comprises detecting if the sub-pool complex kills the cell.

* * * * *